(12) United States Patent
Wohlrab et al.

(10) Patent No.: US 8,815,077 B2
(45) Date of Patent: Aug. 26, 2014

(54) ELECTROCHEMICAL SENSOR FOR MEASURING THE OXYGEN PARTIAL PRESSURE IN A PROCESS FLUID AND A METHOD FOR TESTING ITS FUNCTION

(75) Inventors: Heinz Wohlrab, Berlin (DE); René Oberlin, Würenlos (CH)

(73) Assignee: Knick Elektronische Messgeräte GmbH & Co. KG, Berlin (DE)

(*) Notice: Subject to any disclaimer, the term of this patent is extended or adjusted under 35 U.S.C. 154(b) by 181 days.

(21) Appl. No.: 13/388,828

(22) PCT Filed: Jun. 23, 2010

(86) PCT No.: PCT/EP2010/058915
§ 371 (c)(1),
(2), (4) Date: Feb. 3, 2012

(87) PCT Pub. No.: WO2011/015407
PCT Pub. Date: Feb. 10, 2011

(65) Prior Publication Data
US 2012/0125790 A1  May 24, 2012

(30) Foreign Application Priority Data
Aug. 4, 2009 (DE) .......................... 10 2009 036 012

(51) Int. Cl.
*G01N 27/40* (2006.01)
(52) U.S. Cl.
USPC ........ 205/783; 205/782; 205/782.5; 204/431; 204/229.7; 204/415
(58) Field of Classification Search
CPC ....... G01N 27/30; G01N 27/40; G01N 27/48; G01N 27/404; G01N 27/403; G01N 27/4163; G01N 33/5438
USPC ............... 204/431, 432, 415, 229.7; 205/782, 205/782.5, 783, 793
See application file for complete search history.

(56) References Cited

U.S. PATENT DOCUMENTS 4,450,064 A  5/1984  Harman, III
4,518,477 A  5/1985  Wright et al.
(Continued)

FOREIGN PATENT DOCUMENTS

DE  197 26 453 A1  1/1999
DE  198 45 318 C2  9/2000
(Continued)

*Primary Examiner* — J. Christopher Ball
(74) *Attorney, Agent, or Firm* — McGlew and Tuttle, P.C.

(57) ABSTRACT

An electrochemical sensor for measuring the oxygen partial pressure in a process fluid, comprises
an electrolyte-filled sensor body, which is covered on one side charged with the process fluid by an oxygen-permeable membrane,
a cathode on the membrane,
an annular guard electrode surrounding the cathode, which in measuring operation lies at the same potential as the cathode,
an anode charged by the electrolyte in the sensor body,
a reference electrode charged by the electrolyte in the sensor body, wherein between the anode and cathode a voltage can be applied, which is controlled between the cathode (8) and reference electrode at a constant polarization voltage and the measuring sensor current flowing in measuring operation between the cathode and anode is a measure for the oxygen partial pressure in the process fluid, and
a test voltage source which can be switched in a testing mode between the cathode and guard electrode for producing test oxygen in the electrolyte and/or in the process fluid between the cathode and guard electrode for testing the function of the sensor.

13 Claims, 2 Drawing Sheets

(56) References Cited

U.S. PATENT DOCUMENTS

| | | |
|---|---|---|
| 5,098,547 A | 3/1992 | Bryan et al. |
| 5,668,302 A | 9/1997 | Finbow et al. |
| 7,175,753 B2 | 2/2007 | Kiesele et al. |
| 7,704,356 B2 | 4/2010 | Kuehn |
| 2006/0219575 A1 | 10/2006 | Oberlin |

FOREIGN PATENT DOCUMENTS

| | | |
|---|---|---|
| DE | 102 15 909 C1 | 10/2003 |
| DE | 10 2005 028 246 B4 | 5/2007 |
| EP | 0 744 620 B1 | 7/2002 |
| EP | 1 707 954 A1 | 10/2006 |
| GB | 2 326 485 A | 12/1998 |
| GB | 2 342 168 A | 4/2000 |

ELECTROCHEMICAL SENSOR FOR MEASURING THE OXYGEN PARTIAL PRESSURE IN A PROCESS FLUID AND A METHOD FOR TESTING ITS FUNCTION

CROSS REFERENCE TO RELATED APPLICATIONS

This application is a United States National Phase application of International Application PCT/EP2010/058915 and claims the benefit of priority under 35 U.S.C. §119 of German Patent Application Serial No. 10 2009 036 012.3 filed Aug. 4, 2009, the entire contents of which are incorporated herein by reference.

FIELD OF THE INVENTION

The invention relates to an electrochemical sensor for measuring the oxygen partial pressure in a process fluid and a method for testing the function of such a sensor.

BACKGROUND OF THE INVENTION

Regarding the background of the invention it should be noted that on measuring the oxygen concentration in process fluids with electrochemical sensors it is necessary to perform a regular check of the functionability of the sensor and the entire measuring device. In particular, with inertisation measurements, in which the oxygen concentrations have to be kept below a maximum level, in order e.g. to avoid ignition or explosion, a regular monitoring of the measuring device is mandatory. An added complication is that electrochemical sensors with a low oxygen concentration only supply a very low measurement current and it is thus difficult to distinguish whether the sensor is defective—e.g. a connection cable is interrupted—or whether in fact the oxygen concentration in the process fluid is very low.

It has previously been usual when checking the function to charge the sensor regularly with a testing gas, such as e.g. air. In addition, it has been necessary to remove the sensor or to use very expensive manual or automatic devices to separate the sensor from the measuring medium and charge it with testing gas.

In this connection it is known from EP 0 744 620 B1 or DE 10 2005 028 246 B4 to equip electrochemical gas sensor arrangements with gas generators, which are operated for checking the sensor itself and produce a testing gas—generally oxygen—in situ, whereby the sensor can be charged with the testing gas and its function can be checked.

The disadvantage of these known gas sensor arrangements is the fact that specifically for the production of testing gas a gas generator has to be provided, which means additional expense for apparatus.

Known electrochemical sensors for measuring the oxygen partial pressure comprise:
  an electrolyte-filled sensor body, which is covered on one side charged with the process fluid by an oxygen-permeable membrane,
  a cathode on the membrane,
  an annular guard electrode surrounding the cathode, which in measuring operation lies at the same potential as the cathode,
  an anode charged by the electrolyte in the sensor body, and
  a reference electrode charged by the electrolyte in the sensor body, wherein between the anode and cathode a voltage can be applied, which can be controlled between the cathode and reference electrode at a constant polarization voltage (potentiostat) and the measuring sensor current flowing in measuring operation between the cathode and anode is a measure for the oxygen partial pressure in the process fluid.

Such sensors usually consist of a three-electrode-arrangement, the mentioned cathode, anode and reference electrode. The purpose of the anode is to keep the potential of the cathode relative to the reference electrode at a stable value, the so-called polarization voltage. The reduction of the oxygen at the cathode causes a current flow from the cathode to the anode which is proportional to the oxygen partial pressure. The whole system is covered by an oxygen-permeable membrane, in order to prevent the exchange of the electrolyte with the measuring medium and other impurities.

When measuring lower oxygen concentrations usually a sensor is used in which the cathode is surrounded by an additional so-called guard ring—this is the guard electrode—, which is at the same potential as the cathode and reduces the remaining oxygen.

SUMMARY OF THE INVENTION

The underlying problem addressed by the invention is to improve an electrochemical sensor of the aforementioned type so that a functional test can be performed by separate gassing with oxygen by avoiding a separate gas generator and the associated cost of apparatus.

This problem is solved in that a test voltage source which can be switched in a testing mode between the cathode and guard electrode is provided which produces test oxygen in the process fluid between the cathode and guard electrode for testing the function of the sensor.

The functionability test of the sensor is thus based on the brief reversal of the polarographic principle. If a positive voltage is applied between the cathode and guard electrode—the positive pole of the test voltage source is connected to the guard electrode—, thus with an aqueous electrolyte at the guard electrode oxygen is produced by oxidation. The thus produced oxygen is reduced after switching off the voltage at the cathode, and this results in an increase of the sensor current. This increase of the sensor current can be evaluated very easily by a measuring device.

By way of these simple measures a regular check of a standard sensor can be performed without spending large amounts on apparatus. A further advantage is the relatively brief interruption of the measurement for the function testing, as the sensor does not have to be removed or there is no need to perform a complicated switching between the measuring medium and testing medium.

According to an additional preferred embodiment of the invention the guard electrode can be switched by a change-over arrangement alternately in testing mode to the test voltage source or directly to the cathode. Said change-over arrangement can have a simple structure and can easily be controlled by means of a corresponding control in the said measuring device.

The invention also relates to a method for testing the function of an electrochemical sensor of the generic type which comprises the following method steps:
  applying a test voltage between the cathode and guard electrode in a testing mode for producing test oxygen in the electrolyte and/or in the process fluid between the cathode and guard electrode,
  switching off the test voltage, and
  evaluating the test sensor current generated by the test oxygen for the function analysis of the sensor.

The above method steps have been explained in detail in relation to the corresponding device.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
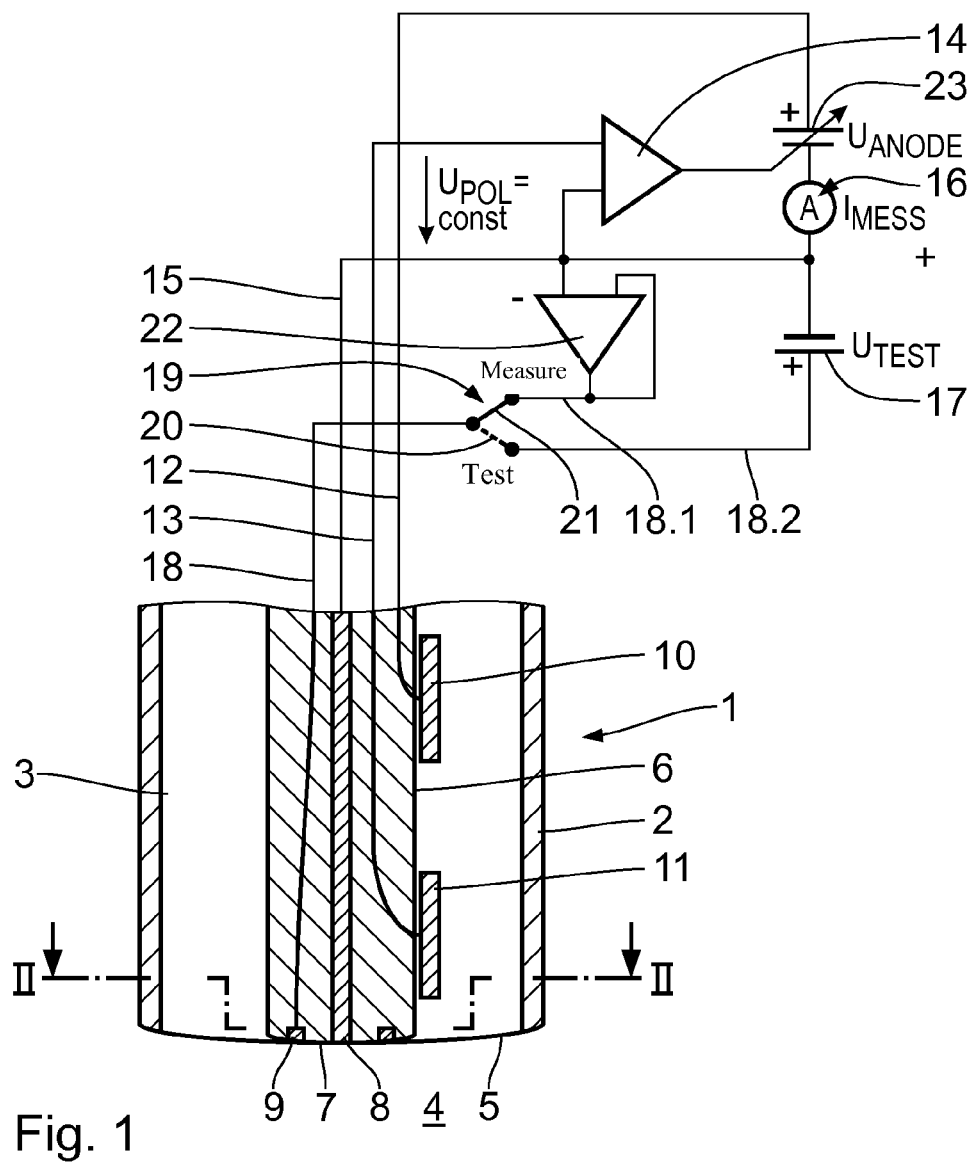
FIG. 1 is a schematic cross sectional view of an electrochemical oxygen sensor with an additional circuit diagram of the measuring circuit and test voltage source.
Figure 2:
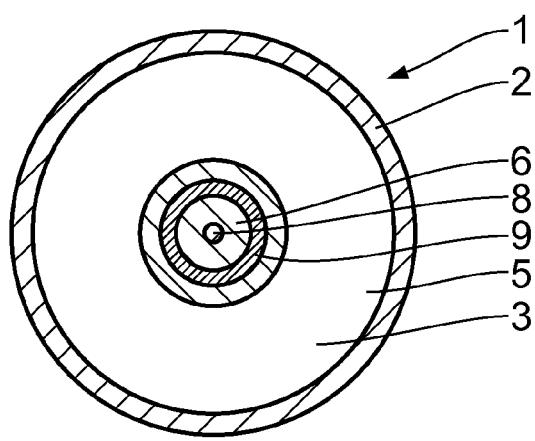
FIG. 2 is a radial cross section of the sensor along the section line II-II of FIG. 1.

As shown clearly from FIGS. 1 and 2, an electrochemical sensor 1 comprises a tubular sensor body 2, which is filled with an electrolyte 3. On the side charged in the measuring operation by a process fluid 4 the electrolyte-filled sensor body 2 is covered by a membrane 5, which is permeable to oxygen, but prevents any exchange between the electrolyte 3 and the process fluid 4.

In a sensor body 2 an electrode holder 6 is arranged axially, which is made from an insulating material. A cathode 8 is formed centrally thereon on the end face side 7, the end face side of which cathode bears against the inner side of the membrane 5. An annular guard electrode 9 lies concentrically around the cathode 8.

An anode 10 and a reference electrode 11 are arranged laterally on the electrode holder 6 inside the sensor body 2.

As shown clearly in the circuit diagram integrated into FIG. 1 the anode 10 and reference electrode 11 can be connected respectively via lines 12, 13 to a potentiostat 14, so that the constant polarization voltage $U_{POL}$ lies between the cathode 8 and reference electrode 11.

The cathode 8 is connected in turn via a line 15, in which a measuring unit 16 is arranged, to the negative pole of the voltage source 23 for the anode voltage $U_{ANODE}$. The measuring sensor current $I_{MESS}$ flowing through the measuring unit 16 is a measure for the oxygen partial pressure in the process fluid 4.

To test the functionability of the sensor arrangement a test voltage source 17 is provided, which can be switched on between the cathode 8 and guard electrode 9 so that its positive pole is connected to the guard electrode 9 via its supply line 18. In this case a change-over arrangement 19 with two alternating opening and closing switches 20, 21 is provided in the line branches 18.1, 18.2 to the voltage source 17 or to the line 15 of the cathode 8. FIG. 1 shows a measuring situation, in which the testing voltage source 17 is disconnected owing to the opened switch 20 and closed switch 21 and the guard electrode 9 is connected via an impedance converter 22 to the cathode 8. This represents the normal measuring state.

For testing the function the change-over switching arrangement 19 is activated so that the two switches 20, 21 change their switching position (shown by dashed lines in FIG. 1) and the test voltage $U_{TEST}$ is applied between the guard electrode 9 and the cathode 8. This causes the production of oxygen from the aqueous electrolyte 3, which is reduced after switching off the voltage $U_{TEST}$ at the cathode 8. This results in an increase in the sensor current $I_{MESS}$.

The path of the measuring sensor current can be detected by the measuring unit 16 integrated for example in a not shown measuring device and evaluated accordingly.

Figure 3:
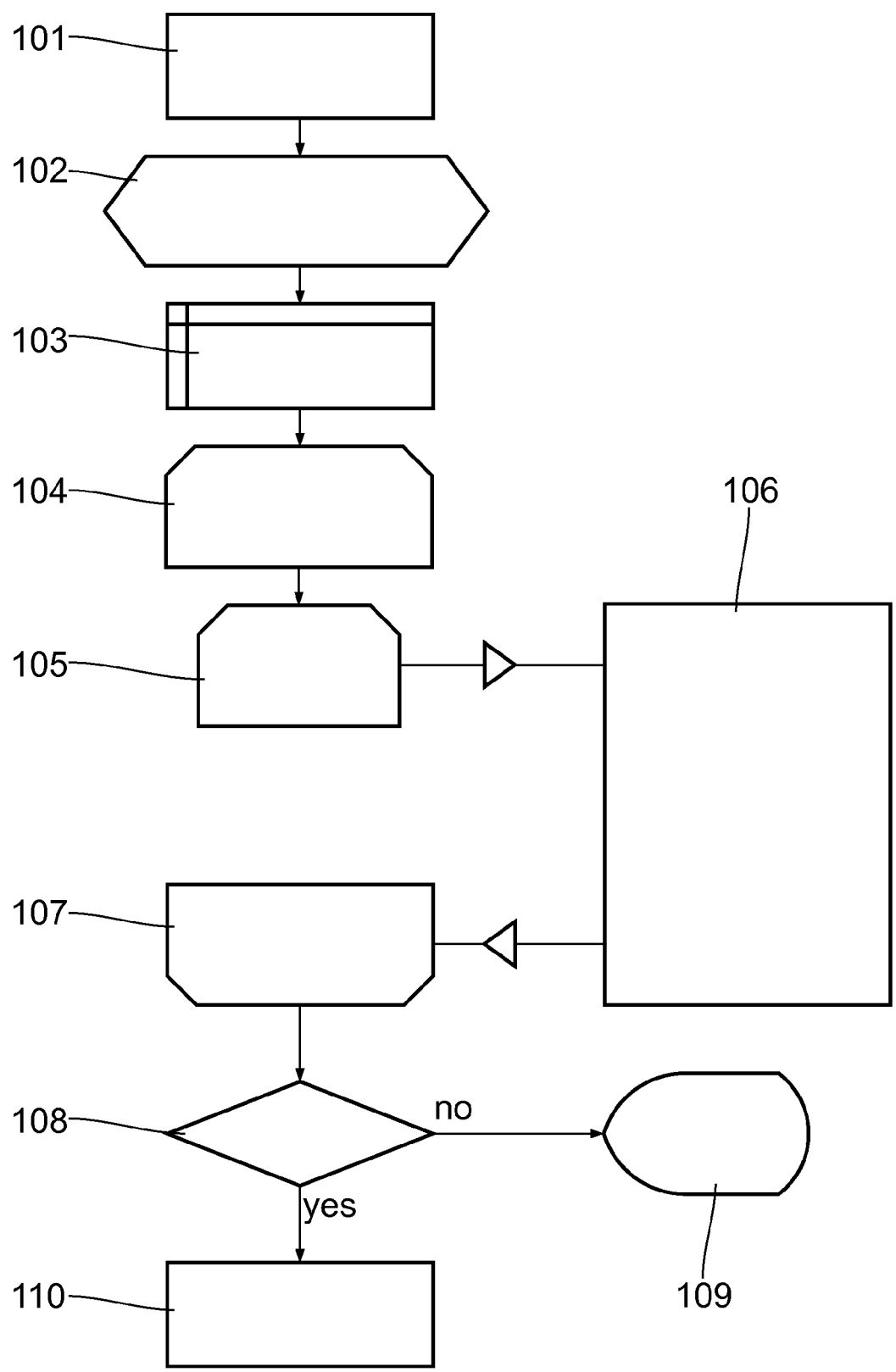
FIG. 3 is a flow diagram of the function test of the sensor.

The method sequence when conducting a corresponding test routine is shown in this connection in FIG. 3. On the basis of the normal oxygen measuring operation shown by block 101 the function testing of the sensor 1 is started by an initialization step 102. In step 103 the last value of the measuring sensor current $I_{MESS}$ is stored in a not shown memory. Afterwards in step 104 the test voltage $U_{TEST}$ is applied between the cathode 8 and guard electrode 9. The value of the test voltage and the duration of the increase in potential is in this case sensor-specific.

By means of the measuring unit 16 afterwards in step 105 after switching off the test voltage the measuring sensor current $I_{MESS}$ is determined and—as indicated by block 106—for the functional analysis of the sensor 1 it is evaluated whether the measuring sensor current $I_{MESS}$ has increased accordingly by the additional oxygen input.

From the time dependent development of the fading away of the sensor current and a comparison with the last saved value of the measuring sensor current in a normal state the time point of the reactivation of the measuring operation is calculated. The reactivation is performed if the test sensor current deviates by a specific threshold value from the saved value of the measuring sensor current $I_{MESS}$. The range of the deviations can be for example between 0% and 2%.

At the thus detected time point of the reactivation of the measuring operation the sensor monitoring is ended—step 107—and a query 108 is activated, as to whether the function test of the sensor has resulted in its functionability. If not, a warning and/or message 109 is issued that the sensor is defective. In terms of device safety (SIL regulations) after the detection of a functional error the process installation can be switched off.

If an error-free function has been established the oxygen measurement is continued—step 110.

The application of the test voltage for oxygen production can be achieved otherwise in the aforementioned measuring device, not shown in detail, by simple circuit measures, whereby also in the measuring device itself in a simple manner a time allocation is provided between the oxygen production and the subsequent back measurement.

While specific embodiments of the invention have been shown and described in detail to illustrate the application of the principles of the invention, it will be understood that the invention may be embodied otherwise without departing from such principles.

The invention claimed is:

1. An electrochemical sensor for measuring the oxygen partial pressure in a process fluid, the electrochemical sensor comprising:

an electrolyte-filled sensor body, which is covered on one side charged with the process fluid by an oxygen-permeable membrane;

a cathode on the membrane;

an annular guard electrode surrounding the cathode, which in measuring operation lies at the same potential as the cathode;

an anode charged by the electrolyte in the sensor body;

a reference electrode charged by the electrolyte in the sensor body, wherein between the anode and the cathode a voltage can be applied, which can be controlled between the cathode and the reference electrode at a constant polarization voltage, and wherein the measuring sensor current flowing in measuring operation between the cathode and the anode is a measure for the oxygen partial pressure in the process fluid;

a test voltage source switching in a testing mode between the cathode and the guard electrode to produce test oxygen in at least one of the electrolyte and the process fluid between the cathode and the guard electrode to test the function of the sensor.

2. A sensor according to claim 1, wherein the positive pole of the test voltage source can be connected to the guard electrode.

3. A sensor according to claim 1, wherein in the testing mode the guard electrode can be switched by a change-over switch arrangement alternately to the test voltage source.

4. A sensor according to claim 1, wherein in the testing mode the guard electrode can be switched by a change-over switch arrangement alternately by an impedance converter to the cathode.

5. A method for checking a function of an electrochemical sensor for measuring the oxygen partial pressure in a process fluid, the method comprising:
   providing the electrochemical sensor, the electrochemical sensor comprising:
      an electrolyte-filled sensor body, which is covered on one side charged with the process fluid by an oxygen-permeable membrane;
      a cathode on the membrane;
      an annular guard electrode surrounding the cathode, which in measuring operation lies at the same potential as the cathode;
      an anode charged by the electrolyte in the sensor body; and
      a reference electrode charged by the electrolyte in the sensor body, wherein between the anode and the cathode a voltage is applied, which is controlled between the cathode and the reference electrode at a constant polarization voltage and wherein the measuring sensor current flowing in measuring operation between the cathode and the anode is a measure of the oxygen partial pressure in the process fluid;
   applying a test voltage between the cathode and the guard electrode in a testing mode to produce test oxygen in at least one of the electrolyte and the process fluid between the cathode and the guard electrode;
   switching off the test voltage;
   evaluating the test sensor current generated by the test oxygen for the function analysis of the sensor.

6. A method according to claim 5, wherein the time sequence of the testing sensor current is detected in the testing mode.

7. A method according to claim 6, wherein the value of the measuring sensor current is saved prior to activating the testing mode and the reactivation of the measuring operation is controlled by a comparison of the test sensor current with the saved value of the measuring sensor current.

8. A method according to claim 6, wherein the measuring operation is reactivated if the test sensor current deviates by a specific threshold amount from a saved value of the measuring sensor current.

9. A method according to claim 5, wherein a warning is issued in case of a deviation of the test sensor current from a specified behavior.

10. A method according to claim 5, wherein a reactivation of the measuring operation by the sensor is prevented in case of a deviation of the test sensor current from a specified behavior.

11. An electrochemical sensor for measuring the oxygen partial pressure in a process fluid, the electrochemical sensor comprising:
   an electrolyte-filled sensor body, which is covered on one side charged with the process fluid by an oxygen-permeable membrane;
   a cathode, at least a portion of said cathode being in direct contact with the membrane;
   an annular guard electrode surrounding the cathode, which in measuring operation lies at the same potential as the cathode;
   an anode charged by the electrolyte in the sensor body;
   a reference electrode charged by the electrolyte in the sensor body, wherein between the anode and the cathode a voltage can be applied, which can be controlled between the cathode and the reference electrode at a constant polarization voltage, and wherein the measuring sensor current flowing in measuring operation between the cathode and the anode is a measure for the oxygen partial pressure in the process fluid;
   a test voltage source means for at least producing a test voltage between said cathode and said guard electrode such that said cathode and said guard electrode produce test oxygen to test the function of the sensor.

12. A sensor according to claim 11, wherein the positive pole of the test voltage source can be connected to the guard electrode.

13. A sensor according to claim 11, wherein in the testing mode the guard electrode can be switched by a change-over switch arrangement alternately to the test voltage source.

* * * * *